United States Patent
Kang et al.

(10) Patent No.: US 7,982,050 B2
(45) Date of Patent: Jul. 19, 2011

(54) PROCESS FOR PREPARING LIGANDS OF PPARDELTA AND THE INTERMEDIATE COMPOUNDS FOR PREPARING THE SAME

(75) Inventors: Heon Joong Kang, Kyeongki-do (KR); Jung Yeob Ham, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 338 days.

(21) Appl. No.: 11/913,822

(22) PCT Filed: May 7, 2005

(86) PCT No.: PCT/KR2005/001341
§ 371 (c)(1),
(2), (4) Date: May 30, 2008

(87) PCT Pub. No.: WO2006/121223
PCT Pub. Date: Nov. 16, 2006

(65) Prior Publication Data
US 2009/0118516 A1    May 7, 2009

(51) Int. Cl.
*C07D 277/26* (2006.01)
(52) U.S. Cl. ........................................ 548/203
(58) Field of Classification Search .............. 548/203, 548/235
See application file for complete search history.

(56) References Cited

U.S. PATENT DOCUMENTS

| 6,723,740 B2 * | 4/2004 | Chao et al. | 514/365 |
| 2003/0207924 A1 * | 11/2003 | Cheng et al. | 514/365 |

FOREIGN PATENT DOCUMENTS

| WO | 02/092590 | 11/2002 |
| WO | 03/074504 | 12/2003 |
| WO | 03/106442 | 12/2003 |

OTHER PUBLICATIONS

Document No. 139:230769, retrieved from CAPLUS, Jun. 2010.*
Document No. 136:304064, retrieved from CAPLUS, Jun. 2010.*

* cited by examiner

*Primary Examiner* — Shawquia E Young
(74) *Attorney, Agent, or Firm* — Lowe Hauptman Ham & Berner LLP

(57) ABSTRACT

The present invention provides a process for preparing thiazole derivatives of formula (I), that activate the delta subtype of the human Peroxisome Proliferator Activated Receptor (hPPAR δ), and also provides compounds of formula (II), (IV), (X), (XI) and (XII), intermediate compounds for preparation of the above compounds of formula (I).

2 Claims, No Drawings

PROCESS FOR PREPARING LIGANDS OF PPARDELTA AND THE INTERMEDIATE COMPOUNDS FOR PREPARING THE SAME

TECHNICAL FIELD

The present invention relates to a process for preparing thiazole derivative of formula (I), that activates the delta subtype of the human Peroxisome Proliferator Activated Receptor (hPPAR δ), and also relates to the compounds of formula (II), (IV), (X), (XI) and (XII), intermediate compounds for preparation of the above compound of formula (I).

BACKGROUND ART

Especially, 2-{2-methyl-4-[({4-methyl-2-[4-(trifluoromethyl)phenyl]-1,3-thiazole-5-yl}methyl)sulfanyl]phenoxy}acetic acid (hereinafter, called to "GW501516") among thiazole derivatives of formula (I) showed an excellent effect to treatment of obesity in animal models (*Cell* 2003, 113, 159), and proved effectiveness in cardiovascular disease by increasing high density lipoprotein (HDL) and decreasing low density lipoprotein (LDL) effectively in the animal experiment (*Proc. Natl. Acad. USA* 2001, 98, 5306) and in clinical trial. And the process for preparation of the said substance has been disclosed in PCT publication WO 01/00603A 1, *Bioorg. Med. Chem. Lett.* 2003, 13, 1517 and *J. Chem. Org.* 2003. 68. 9116, in which GW501516 (13) was prepared, as shown in the following scheme (1). Methyl (4-mercapto-3-methylphenoxy)acetate (7), synthesized from the starting material, 4-hydroxy-3-methylacetophenone (1), via 6 steps, was coupled to 5-chloromethyl-4-methyl-2-(4-trifluoromethyl-phenyl)thiazole (11), which was prepared from 4-(trifluoromethyl)thiobenzamide (8) via 3 steps, in the presence of excessive cesium carbonate to obtain the methyl ester (12) of GW501516, and then treating the ester with 1 N lithium hydroxide to give GW501516.

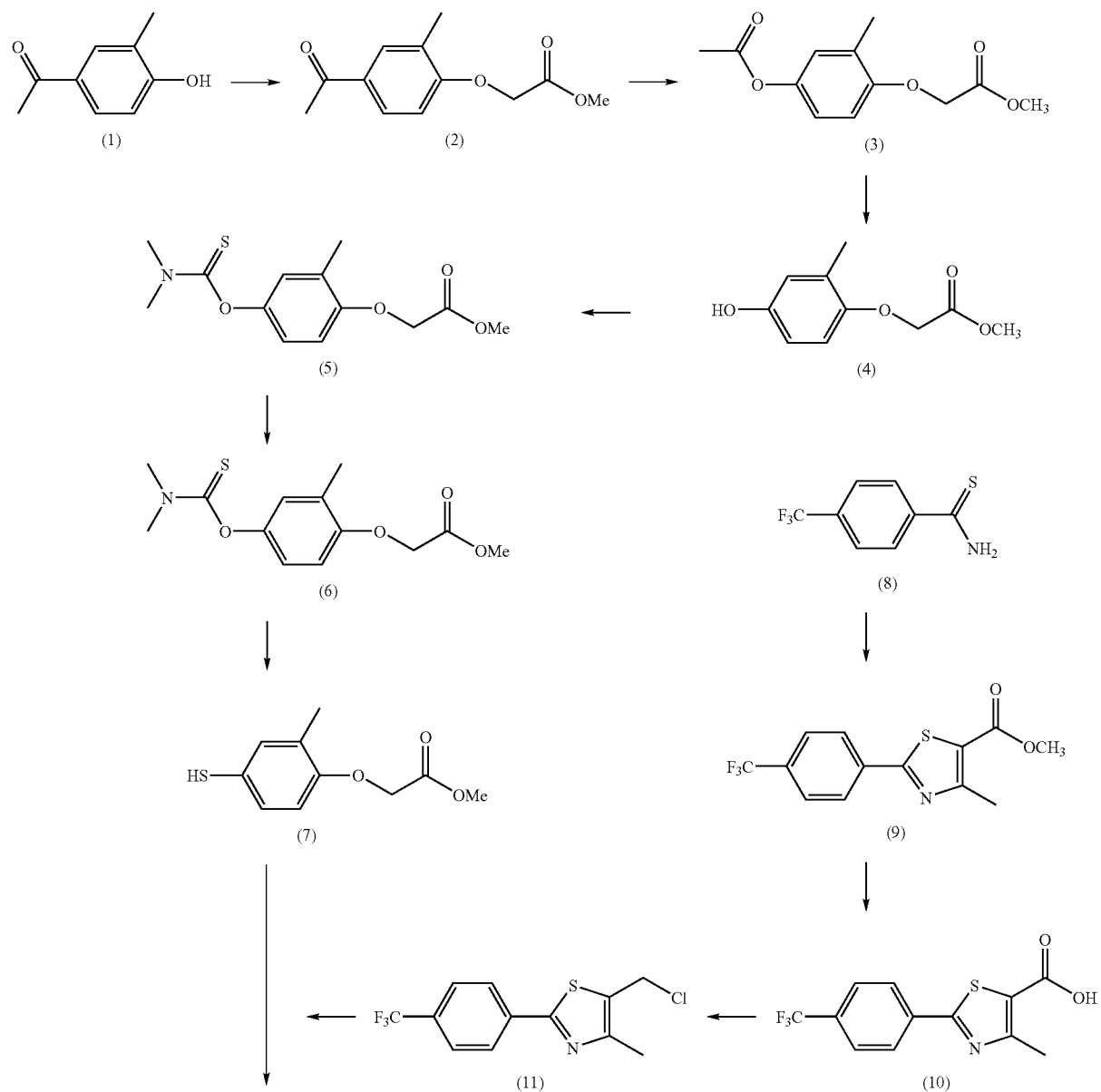

Reaction scheme (1)

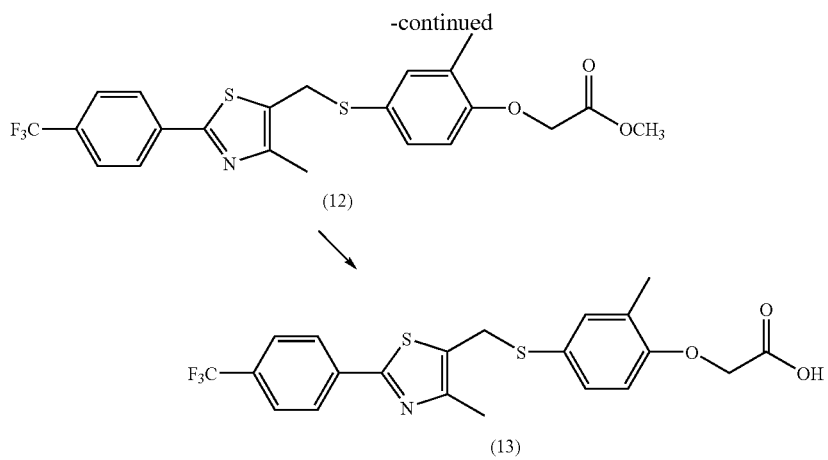

As an alternative synthesis method of GW501516, it is disclosed, as illustrated in the following scheme (2), that the compound (13) of GW501516 can be prepared by introducing ethyl acetate group to o-cresol (14), reacting the resulted compound (15) with sulfonyl chloride, reducing the resulted compound (16) with tin (Sn) under acidic condition to form ethyl (4-mercapto-2-methyl phenoxy)acetate (17), reacting it with 5-chloromethyl-4-methyl-2-(4-trifluoromethyl phenyl) thiazole (11) together with an excessive cesium carbonate to obtain the ethyl ester intermediate (18) of GW501516, and deprotecting the ester group of the intermediate compound with 1N lithium hydroxide.

Reaction scheme (2)

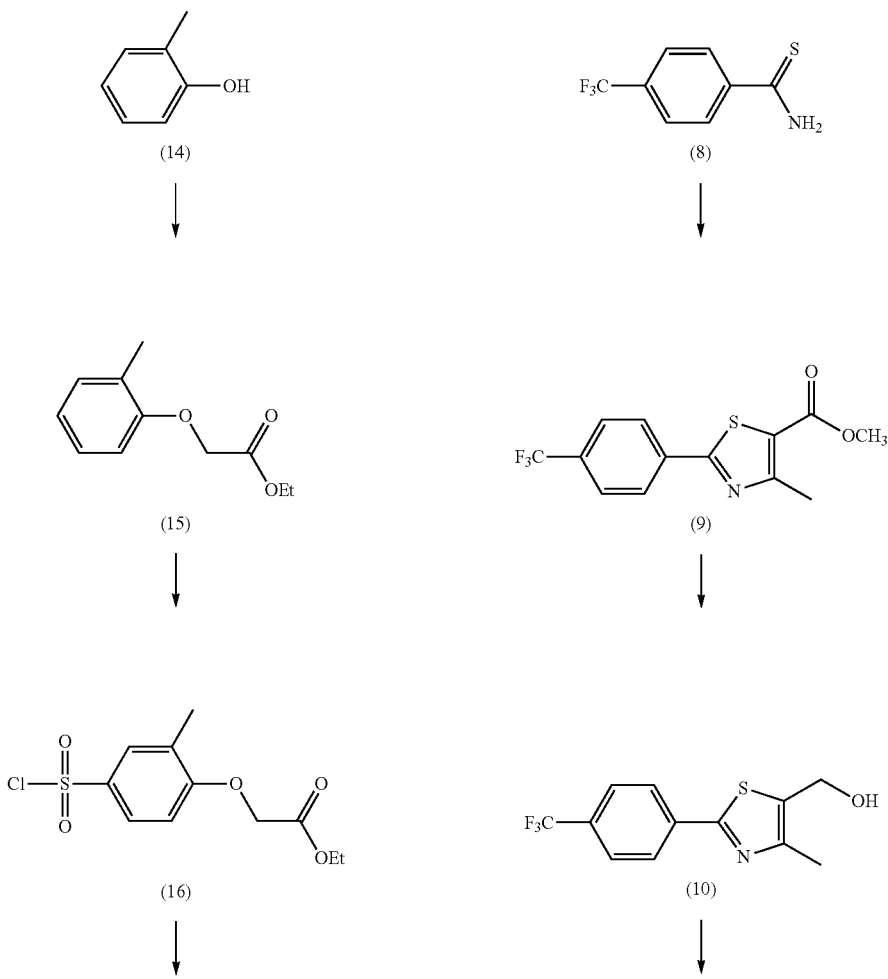

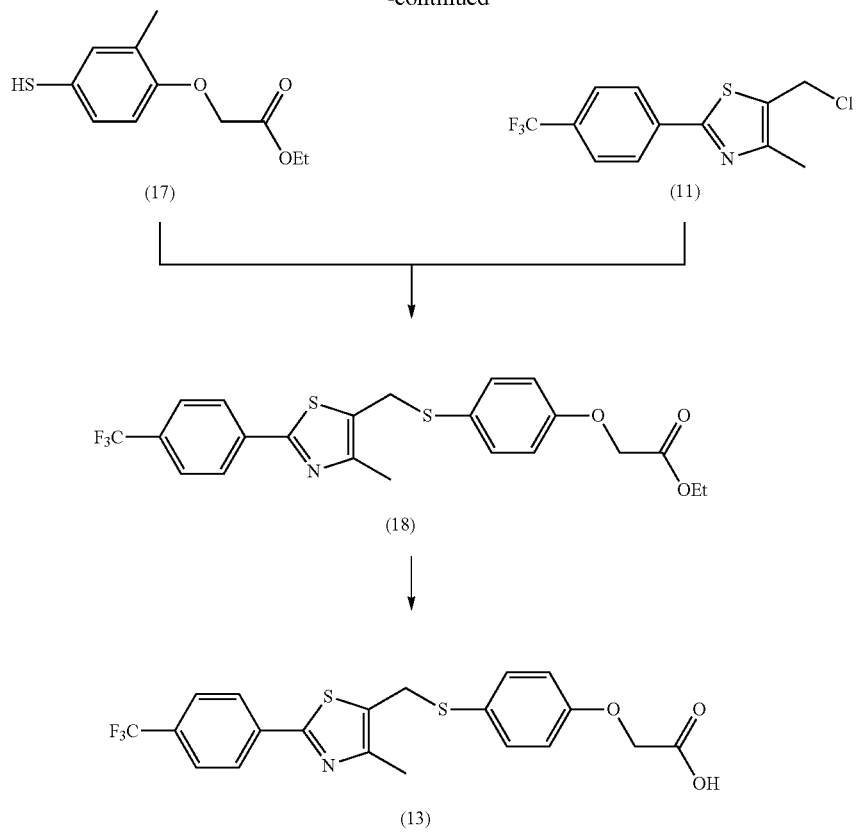

As another alternative synthesis method of GW501516, it is disclosed, as illustrated in the following scheme (3), that the compound (13) of GW501516 can be prepared by reacting o-cresol with sodium thiocynate in the presence of bromine, reducing the resulted compound with lithium aluminium hydride to form 4-mercapto-2-methylphenol (20), reacting it with 5-chloromethyl-4-methyl-2-(4-trifluoromethyl phenyl) thiazole (11) and methylbromoacetate sequentially to obtain the ethyl ester intermediate (12) of GW501516, and deprotecting the ester group of the intermediate compound with 2 M lithium hydroxide.

Reaction scheme (3)

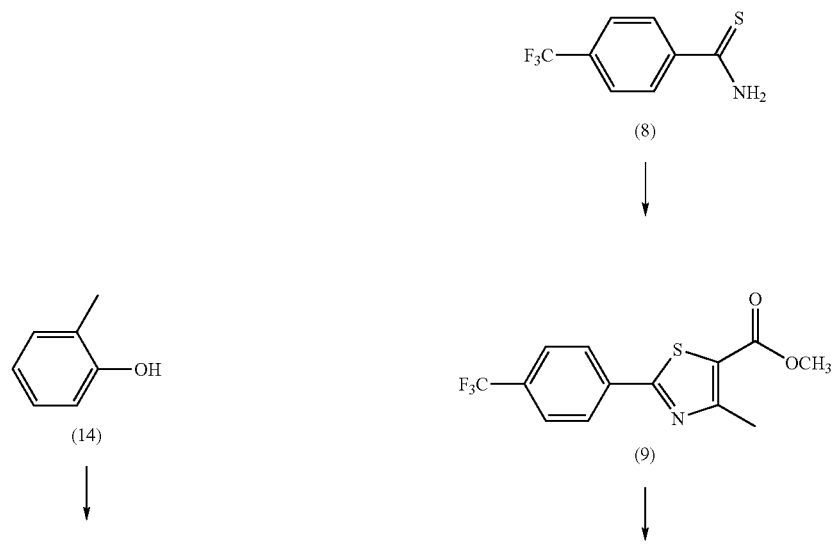

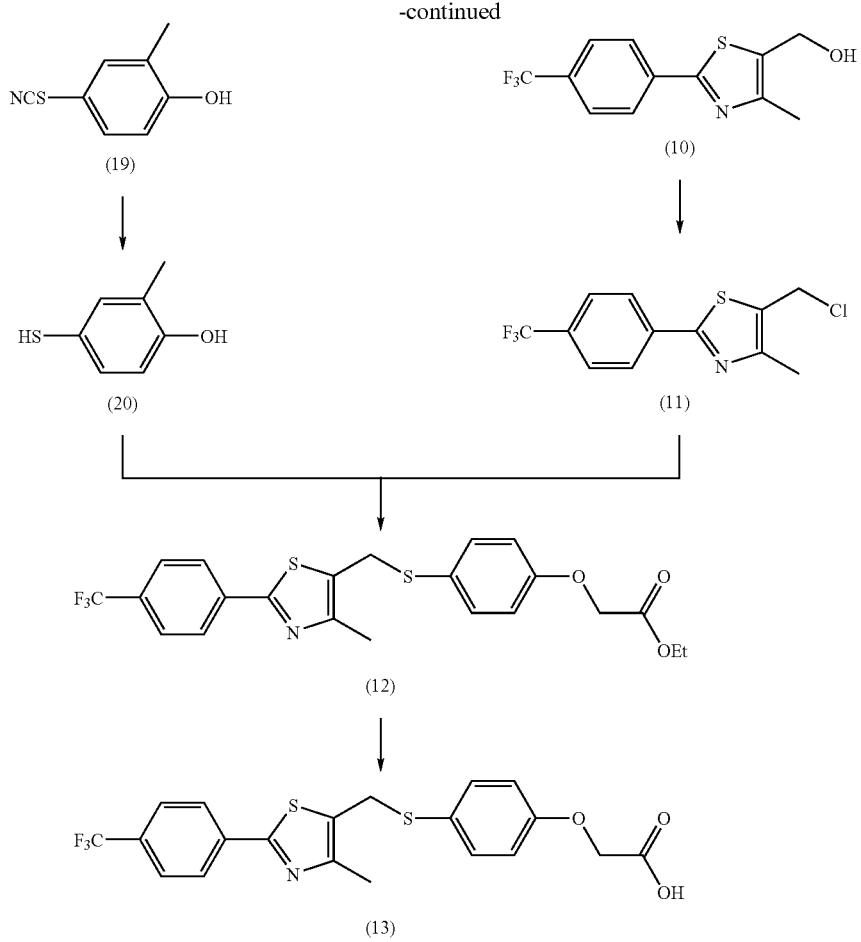

DISCLOSURE OF THE INVENTION

Although the above compound (13) has known to be an excellent efficacy in the treatment of obesity in animal models and in the treatment of disease states associated with cholesterol metabolism in clinical trials, the manufacturing method thereof was not satisfactory, thereby being not cost-effective. That is to say, 1) The manufacturing method of reaction scheme (1) consists of 12 steps, and the total yield thereof is as low as 2%. So, it is not proper to be applied to the industry, due to its extreme low production yield.
2) The manufacturing process according to the reaction scheme (1) includes three refluxing steps at elevated temperature for 16 hours, which takes long time to obtain the final product.
3) Tin (Sn) powder used in reaction scheme (2) is very unstable to the moisture, and moreover, it is a combustible metal, thereby being very dangerous to adopt it in industrial scale.
4) An excessive tin (Sn) powder used in the reaction scheme (2) may lead to pollution of the environment.
5) Bromine ($Br_2$) used in the reaction scheme (3) may lead to pollution of environment.
6) A separated another step for reacting compound (11) with compound (7), (17) or (20) in the reaction scheme (1), (2) or (3) is required, and also an excess amount of cesium carbonate, which is not common inorganic base, is used, and also the reaction time is comparatively long.
7) The hydrolysis steps of methyl or ethyl ester using 1 N lithium hydroxide in reaction scheme (1) or (2) requires a long reaction time, about 16 hours, of which yield is as low as 60%.
8) Methyl or ethyl (4-mercapto-2-methylphenoxy)acetate (7), (17) or 4-mercapto-2-methylphenol (20) obtained as an intermediate compound in the reaction scheme (1), (2) or (3) is unstable, so the respective compound can be easily changed to disulfides, which results in lowering the total reaction yield.

Under the circumstance, the novel process for preparing the above compound with easiness and low cost has been demanded in the art.

In view of the above situation, the inventors of the present invention have conducted extensive studies on the novel processes for preparing compounds of the following formula (I). As a result, the inventors have found that the said compounds can be prepared in a high yield and high purity by reacting compounds of formula (II) with alkyl halogen acetate of formula (III) to form compounds of formula (IV) and hydrolyzing the resulting compounds, as shown in the following reaction scheme.

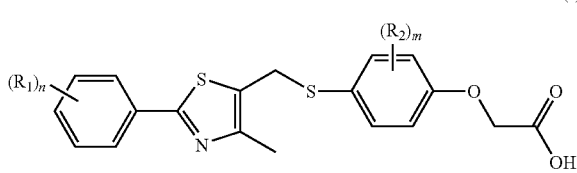
(I)

-continued

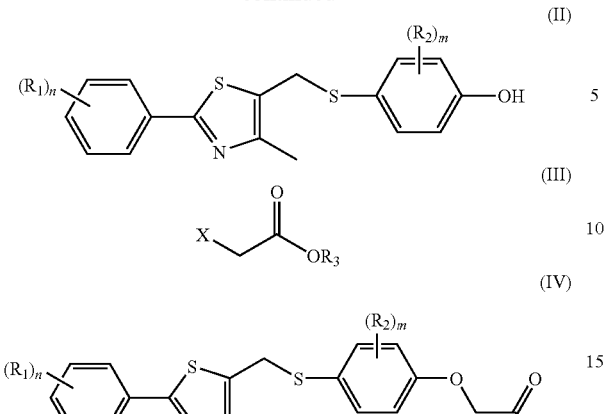

wherein, $R_1$ represents a hydrogen atom, halogen atom or $CF_3$, $R_2$ represents a hydrogen atom, fluorine atom, chlorine atom, —$(C_1$-$C_4)$ alkyl, —O$(C_1$-$C_4)$ alkyl, —S$(C_1$-$C_4)$ alkyl or —N$(C_1$-$C_4$ alkyl$)_2$ group, $R_3$ represents carboxlic protecting group having —$(C_1$-$C_4)$ alkyl group such as methyl, ethyl, propyl, isopropyl, butyl or tert-butyl group, X represents a halogen atom, m is an integer of 0 to 4, n is an integer of 0 to 5.

An object of the present invention is to provide a process for preparing compounds of formula (I) in a high yield in a short period, via unstable intermediate compounds without separation step in the reaction.

The present invention also provides a process for preparing compounds of formula (VI) for preparing compounds of formula (II), which comprises by reacting compounds of formula (V) with alkyl 2-chloroacetoacetate.

The present invention further provides a process for preparing compounds of formula (VII) for preparing compounds of formula (II), which comprises by reducing the ester moiety of compounds of formula (VI).

The present invention further provides a process for preparing compounds of formula (VIII) for preparing compounds of formula (II), which comprises by introducing a leaving group, which is reactive to alcohols, to compounds of formula (VII).

The present invention further provides a process for preparing compounds of formula (X), which comprises by reacting compounds of formula (IX) with Grignard reagents.

The present invention further provides a process for preparing compounds of formula (II), a starting material of the present invention, which comprises by reacting compounds of formula (X) with organometallic reagents and sulfur ($S_8$) to form compounds of formula (XI) and (XII) sequentially, and reacting them with compounds of formula (VIII) without a specific organic or inorganic base.

The present invention further provides novel compounds of formula (II), (IV), (X), (XI) and (XII), each of which useful as intermediate compounds for preparation of the final products of the present invention.

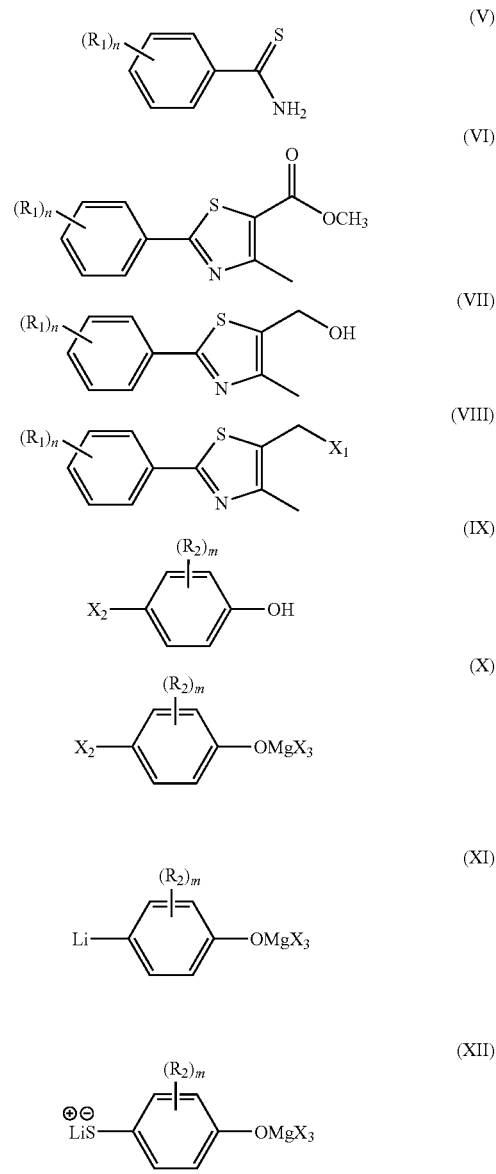

[wherein, $R_1$, $R_2$, $R_3$, n and m have the same definitions as described above]

$X_1$ represents a leaving group. A generally used leaving group is preferred, such as a halogen atom, methanesulfonate (MsO—), and p-toluenesulfonate (TsO—). Here, a halogen atom means a fluorine atom, chlorine atom, bromine atom or iodine atom. Of these, a halogen atom is preferred, with a chlorine atom, bromine atom and iodine atom being particularly preferred.

Example of the halogen atom represented by $X_2$ includes a fluorine atom, chlorine atom, bromine atom or iodine atom. Of these, a bromine atom and iodine atom are preferred.

$X_3$ represents a halogen atom forming Grignard reagents such as a chlorine atom or bromine atom.

The compounds of the formula (V) and (IX), which are used for preparing the starting material (II), are commercially available or can be synthesized easily by using known methods in the art.

BEST MODE FOR CARRYING OUT THE INVENTION

The process of the present invention will be described as set below.

[Step A] Preparation of Compounds of Formula (VI):

Compounds of formula (VI) can be prepared by reacting compounds of formula (V) with ethyl or methyl 2-chloroacetoacetate in a solvent.

Suitable solvents usable in this reaction include alcohols such as methanol, ethanol, propanol, and butanol; and ethers such as diethyl ether, tetrahydrofuran, and 1,4-dioxane. Of these, ethanol or tetrahydrofuran is preferred as a solvent.

The reaction time and temperature depend on the solvent to be used. However, it is preferred to conduct the reaction at 25 to 150° C. for 6 hours to 1 day, more preferably 60 to 120° C. within 16 hours.

[Step B] Preparation of Compounds of Formula (VII):

Compounds of formula (VII) can be prepared by reducing the ester moiety of compounds of formula (VI) in an anhydrous solvent.

As reducing agents, aluminum hydrides such as lithium aluminum hydride, and diisobutylaluminum hydride, and boron hydrides such as sodium borohydride and lithium borohydride can be given. Among them, lithium aluminum hydride and diisobutylaluminum hydride are preferred.

As anhydrous solvents usable in this reaction, diethyl ether, tetrahydrofuran, and dichloromethane can be given, with preferably, dichloromethane.

The reaction time and temperature depend on the solvent to be used. However, it is preferred to conduct the reaction at −100 to 60° C. for 30 minutes to 6 hours, more preferably −78 to 25° C. within 2 hours.

[Step C] Preparation of Compounds of Formula (VIII):

Compounds of formula (VIII) can be prepared by subjecting halogenation reaction on compounds of formula (VII), or reacting compounds of formula (VII) with methanesulfonyl chloride or p-toluene sulfonyl chloride in a solvent.

Suitable solvents usable in this reaction include N,N-dimethylformamide, diethyl ether, tetrahydrofuran, tetrachloromethane, chloroform, dichloromethane, and pyridine. Of these, dichloromethane for halogenation reaction, and pyridine for methanesulfonate or p-toluenesulfonate reaction respectively are preferred.

Suitable reagents for halogenation reaction to the alcohol moiety include triphenylphosphine (TPP) with N-chlorosuccinimide (NCS), triphenylphosphine with chlorine gas, triphenylphosphine with tetrachloromethane ($CCl_4$), phosphorus pentachloride ($PCl_5$), thionylchloride ($SOCl_2$), and methanesulfonyl chloride ($MeSO_2Cl$) for introduction of chlorine atom; triphenylphosphine with N-bromosuccinimide (NBS), triphenylphosphine with bromine gas, triphenylphosphine with tetrabromomethane ($CBr_4$), phosphorus pentabromide ($PBr_5$), and thionyl bromide ($SOBr_2$) for introduction of bromine atom; triphenylphosphine with N-iodosuccine imide (NIS), triphenylphosphine with solid iodine, and triphenylphosphine with tetraiodomethane ($CI_4$) for introduction of iodine atom. Alternatively, introduction of iodine atom can be carried out by substituting chloro- or bromocompounds of formula (VIII) with sodium iodide (NaI) in acetone, so-called halogen-iodine substitution method. Methanesulfonyloxy group or p-toluenesulfonyloxy group can be introduced by a reaction with methanesulfonyl chloride or p-toluene sulfonyl chloride in a pyridine solvent. Of these, the preferred leaving group is chlorine or bromine atom, and the preferred reagent for this reaction is triphenylphosphine with N-chlorosuccinimide or N-bromosuccinimide.

The reaction time and temperature depend on the solvent to be used. However, it is preferred to conduct this reaction at −10 to 40° C. for 30 minutes to 1 day, more preferably 10 to 25° C. within 2 hours.

[Step D] Preparation of Compounds of Formula (II) from Compounds of Formula (VIII) and (XII):

Compounds of formula (II) can be prepared by protecting phenol groups of compounds of formula (IX) with Grignard reagents, reacting them with organometallic reagents and sulfur sequentially, and then reacting the resulted compounds with compounds of formula (VIII). This reaction comprises four step reactions, which are conducted at once.

[Step D-1] Preparation of Compounds of Formula (X) from Compounds of Formula (IX):

Suitable anhydrous solvents usable in this reaction include diethyl ether, tetrahydrofuran, hexane, and heptane. These solvents may be used either singly or in combination of two or more. Of these, a solvent in combination of diethyl ether and tetrahydrofuran is preferred.

Suitable Grignard reagents usable in this reaction include methyl-, ethyl-, n-propyl-, isopropyl-, n-butyl- and isobutyl-magnesium chloride ($R_2MgCl$) or bromide ($R_2MgBr$). Of these, isopropyl magnesium chloride or bromide is preferred.

The reaction time and temperature depend on the solvent to be used. However, it is preferred to conduct this reaction at 20 to 40° C. for 10 to 60 minutes, more preferably at 0 to 25° C. for 10 to 30 minutes.

[Step D-2] Preparation of compounds of formula (XI) from compounds of formula (X) and [Step D-3] Preparation of compounds of formula (XII) from compounds of formula (XI):

As suitable organometallic reagents used for halogen-metal substitution, n-butyl lithium, sec-butyl lithium, and tert-butyl lithium can be used. Of these, tert-butyl lithium is preferred.

Suitable sulfur usable in this reaction is fine sulfur powder and it is preferred to dissolve sulfur in solvents and add it slowly.

The reaction time and temperature depend on the solvent to be used. However, it is preferred to conduct this reaction at −78 to 25° C., more preferably in the step of halogen-metal substitution at −75° C. for 10 to 30 minutes and in the step of sulfur introduction at −75° C., later raising the reaction temperature up to 0° C. for 30 to 90 minutes.

[Step D-4] Preparation of compounds of formula (II) from compounds of formula (VIII) and (XII):

Suitable halogen atoms of 5-halogenmethyl-4-methyl-2-[4-(trifluoromethyl)phenyl]thiazole of formula (VIII) usable in this reaction include a chlorine atom, bromine atom, and iodine atom, preferably a chlorine atom.

The reaction time and temperature depend on the solvent to be used. However, it is preferred to conduct this reaction at −78 to 25° C. for 10 to 120 minutes, more preferably at 0 to 10° C. for 10 to 60 minutes.

[Step E] Preparation of Compounds of Formula (IV).

Compounds of formula (IV) can be prepared by reacting compounds of formula (II) with alkyl halogen acetates of formula (III) in the presence of a base in a solvent.

The alkyl halogen acetates are commercially available or can be synthesized by known methods in the art. The alkyl group and halogen therein include methyl, ethyl, tert-butyl and a chlorine atom, bromine atom, and iodine atom, respectively. The most preferred one among the alkyl halogen acetates is methyl (or ethyl) chloro (or bromo) acetate.

Suitable solvents usable in this reaction include N,N-dimethylformamide, N,N-dimethylacetamide, dimethyl sulfoxide (DMSO), acetonitrile. These solvents may be used either singly or in combination with 1 to 10% water. Of these, acetone and dimethyl sulfoxide including 5% water are preferred.

There is no specific limitation to bases used regardless of basicity, inasmuch as the base does not affect the reaction. Suitable bases include alkali metal hydrides such as sodium hydride, lithium hydride, potassium hydride; alkali metal hydroxide such as sodium hydroxide, potassium hydroxide and alkali metal carbonate such as lithium carbonate, sodium carbonate, sodium bicarbonate, potassium carbonate, and potassium bicarbonate. Of these, alkali metal hydride or alkali metal carbonate is preferred, with potassium carbonate being particularly preferred.

Although there is no specific limitation to the reaction temperature within the boiling point of the solvent to be used, the reaction at a relatively high temperature is not preferred. It is preferred to conduct this reaction at 0 to 60° C. The reaction time depends on the reaction temperature, however, it is preferred to conduct this reaction for 30 minutes to 1 day, more preferably for 30 to 90 minutes.

[Step F] Preparation of Compounds of Formula (I).

Compounds of formula (I) can be prepared by subjecting hydrolysis of the carboxylic ester of compounds of formula (IV) in the presence of a water-soluble inorganic base and alcohol solvent.

Suitable solvents usable in this reaction include methanol, ethanol, and water miscible organic solvents.

As a base usable in this reaction, about 0.1 to 6 N aqueous solution of alkali metal hydroxide, such as lithium hydroxide, sodium hydroxide, or potassium hydroxide, is used. Of these, 1 to 3 N sodium hydroxide is preferred.

The reaction time and temperature depend on the solvent to be used. However, it is preferred to conduct this reaction at −10 to 80° C. for 10 minutes to 3 hours, more preferably 0 to 25° C. for 30 minutes to 1 hour.

Compounds of formula (I) obtained as above are ligands of the human PPAR protein, PPARδ.

EXAMPLES

The present invention will next be described in detail by way of examples, which should not be construed as limiting the invention.

Example 1

Preparation of methyl 4-methyl-2-[4-(trifluoromethyl)phenyl]thiazole-5-carboxylate [Step A]

4-(Trifluoromethyl)thiobenzamide (20.5 g, 0.1 mol) was dissolved in tetrahydrofuran (300 ml) at room temperature, and then methyl 2-chloroacetoacetate (12.2 ml, 0.1 mol, 1.0 eq.) was added slowly for about 20 minutes therein while stirring. After completion of addition, the mixture was stirred again at room temperature for 30 minutes, and then the mixture was heated and refluxed at 75 to 80° C. for 12 hours. After completion of the reaction, the reaction mixture was cooled to room temperature. Subsequently, 50% aqueous solution of sodium hydroxide (150 ml) was added and stirred for 20 minutes. The resultant organic layer was separated by extraction with brine and ethyl acetate, and dried over magnesium sulfate. The solvent was evaporated under reduced pressure to thereby yield 28.8 g of the title compound (yield: 95.6%).

$^1$H-NMR (300 MHz, CDCl$_3$): 8.01 (d, 2H, J=8.4 Hz), 7.64 (d, 2H, J=8.3 Hz), 3.84 (s, 3H), 2.73 (s, 3H).

Example 2

Preparation of [4-methyl-2-(4-trifluoromethyl-phenyl)thiazole-5-yl]-methanol [Step B]:

Methyl 4-methyl-2-[4-(trifluoromethyl)phenyl]]thiazole-5-carboxylate (20.0 g, 66.4 mmol) obtained from Example 1 was dissolved in anhydrous dichloromethane (500 ml) under nitrogen atmosphere, and the reaction mixture was cooled to −78° C. Diisobutyl aluminum hydride (DIBAL-H, 166 ml, 1.0 M hexane solution, 2.5 eq.) was slowly added to the solution for 30 minutes, and the mixture was reacted for another 30 minutes at the same temperature. Subsequently, the temperature was raised to −10° C. and reacted for 30 minutes. After completion of the reaction, an excessive diisobutyl aluminum hydride was removed by ethyl acetate. The resultant residue was extracted by 10% sulfuric acid and ethyl acetate, followed by drying over magnesium sulfate. The resultant mixture was evaporated under reduced pressure to thereby yield 17.5 g of the title compound (yield: 96.4%).

$^1$H-NMR (300 MHz, CDCl$_3$): 7.94 (d, 2H, J=8.1 Hz), 7.63 (d, 2H, J=8.2 Hz), 4.80 (s, 2H), 2.93 (bs, 1H), 2.41 (s, 3H).

$^{13}$C-NMR (78.5 MHz, CDCl$_3$): 164.6, 151.0, 137.0, 133.1, 132.0 (q, J=33 Hz), 126.8, 126.3 (q, J=4 Hz), 122.5, 57.1, 15.4.

Example 3

Preparation of 5-bromomethyl-4-methyl-2-[(4-trifluoromethyl)phenyl]thiazole [Step C]:

[4-Methyl-2-(4-trifluoromethyl-phenyl)thiazole-5-yl] methanol (15.0 g, 55.0 mmol) obtained from Example 2 was dissolved in anhydrous dichloromethane (300 ml), and then triphenylphosphine (TPP, 15.7 g, 60.0 mmol, 1.1 eq.) and tetrabromomethane (20.0 g, 60.0 mmol, 1.1 eq.) were added to the mixture sequentially at room temperature. After stirring for 1 hour, the solvent was evaporated from the reaction mixture under reduced pressure. Subsequently, the remained triphenylphosphine oxide was precipitated by a mixed solvent of hexane and ethyl acetate (v/v=5/1), followed by filtration and evaporation under reduced pressure to thereby yield 17.2 g of the title compound (yield: 93%).

$^1$H-NMR (300 MHz, CDCl$_3$): 8.00 (d, 2H, J=8.1 Hz), 7.67 (d, 2H, J=8.2 Hz), 4.72 (s, 2H), 2.47 (s, 3H).

$^{13}$C-NMR (75.5 MHz, CDCl$_3$): 165.0, 153.8, 136.9, 132.4, 129.7 (q, J=33 Hz), 127.0, 126.3 (q, J=4 Hz), 122.5, 23.8, 15.5.

Example 4

Preparation of 5-bromomethyl-4-methyl-2-[(4-trifluoromethyl)phenyl]thiazole [Step C]:

[4-methyl-2-(4-trifluoromethyl-phenyl)thiazole-5-yl] methanol (10.0 g, 36.6 mmol) obtained from Example 2 was dissolved in anhydrous dichloromethane 300 ml, and then triphenylphosphine (TPP, 10.6 g, 40.3 mmol, 1.1 eq.) and N-bromosuccinimide (7.17 g, 40.3 mmol, 1.1 eq.) were added to the mixture sequentially at room temperature. After stirring for 1 hour, the solvent was evaporated from the reaction mixture under reduced pressure. Subsequently, the remained triphenylphosphine oxide was precipitated by a mixed solvent of hexane and ethyl acetate (v/v=5/1), followed by filtration and evaporation under reduced pressure to thereby yield 11.1 g of the title compound (yield: 90.5%).

Example 5

Preparation of 5-chloromethyl-4-methyl-2-[(4-trifluoromethyl)phenyl]thiazole [Step C]:

[4-Methyl-2-(4-trifluoromethyl-phenyl)thiazole-5-yl]methanol (5.0 g, 18.3 mmol) obtained from Example 2 was dissolved in tetrachloromethane (300 ml), and then triphenylphosphine (TPP, 6.3 g, 23.8 mmol, 1.3 eq.) was added and the mixture was stirred under reflux for 10 hours. After completion of the reaction, the temperature of the reactor was cooled to room temperature, and a mixed solvent of hexane and ethyl acetate (v/v=5/1) was added thereto to precipitate the remained triphenylphosphine oxide, followed by filtration and evaporation under reduced pressure to thereby yield 8.4 g of the title compound (yield: 78.4%).

$^1$H-NMR (300 MHz, CDCl$_3$): 8.01 (d, 2H, J=8.1 Hz), 7.68 (d, 2H, J=8.2 Hz), 4.79 (s, 2H), 2.51 (s, 3H).

Example 6

Preparation of 5-chloromethyl-4-methyl-2-[(4-trifluoromethyl)phenyl]thiazole [Step C]:

[4-Methyl-2-(4-trifluoromethyl-phenyl)thiazole-5-yl]methanol (10.0 g, 36.6 mmol) obtained from Example 2 was dissolved in anhydrous dichloromethane (250 ml) and then triphenylphosphine (TPP, 11.5 g, 44.0 mmol, 1.2 eq.) and N-chlorosuccinimide (5.86 g, 44.0 mmol, 1.2 eq.) were added to the mixture sequentially at room temperature. After stirring for 2 hours, the solvent was evaporated under reduced pressure. Subsequently, the remained triphenylphosphine oxide was precipitated by adding a mixed solvent of hexane and ethyl acetate (v/v=5/1), followed by filtration and evaporation under reduced pressure to thereby yield 10.5 g of the title compound (yield: 98.5%).

Example 7

Preparation of 2-Methyl-4-[({4-methyl-2-[(4-trifluoromethyl)phenyl]thiazole-5-yl}methyl)sulfanyl]phenol [Step D]:

4-Iodo-2-methylphenol (11.7 g, 50.0 mmol) was dissolved in anhydrous tetrahydrofuran (400 ml) under nitrogen atmosphere and the temperature was maintained at 0° C. Isopropyl magnesium chloride (27.5 ml, 2M-ether solution, 1.1 eq.) was added to the above mixture slowly and reacted for 10 minutes. After cooling the reaction mixture to −78° C., tert-butyl lithium (64.7 ml, 1.7M-heptane solution, 2.2 eq.) was added slowly and the reaction mixture was reacted for another 20 minutes. A solution of sulfur (1.60 g, 50 mmol, 1.0 eq.) in anhydrous THF (50 ml) was added to the reaction mixture slowly and reacted until the temperature became 0° C. After 60 minutes, the temperature of the reaction mixture was adjusted at 0° C. and 5-chloromethyl-4-methyl-2-[(4-trifluoromethyl)phenyl]-thiazole of formula (VIII) (13.1 g, 45.0 mmol, 0.9 eq.) dissolved in anhydrous THF (40 ml) was added slowly. The reaction mixture was reacted for around 30 minutes, followed by adding aqueous ammonium chloride solution (500 ml) to complete the reaction. The resultant organic layer was separated and dried over magnesium sulfate. The solvent was evaporated under reduced pressure. The residue was purified by silica gel column chromatography (hexane:ethyl acetate=3:1) to thereby yield 16.2 g of the title compound (yield: 91%)

$^1$H-NMR (300 MHz, CDCl$_3$): 7.96 (d, 1H, J=8.2 Hz), 7.64 (d, 2H, J=8.3 Hz), 7.20 (d, 1H, J=1.8 Hz), 6.97 (dd, 1H, J=8.2, 2.2 Hz), 6.59 (d, 1H, J=8.2 Hz) 5.52 (bs, 1H), 4.06 (s, 2H), 2.19 (s, 3H), 2.09 (s, 3H).

$^{13}$C-NMR (75.5 MHz, CDCl$_3$): 164.1, 155.5, 151.7, 137.4, 136.8, 133.6, 131.9 (q, J=33 Hz), 131.8, 131.6, 126.9, 126.4 (q, J=4 Hz), 125.9, 123.8, 115.7, 33.2, 16.2, 14.8

Example 8

Preparation of 2-Methyl-4-[({4-methyl-2-[(4-trifluoromethyl)phenyl]thiazole-5-yl}methyl)sulfanyl]phenol [Step D]:

4-Bromo-2-methylphenol (4.7 g, 25.0 mmol) was dissolved in anhydrous tetrahydrofuran (150 ml) under nitrogen atmosphere and the temperature was maintained at 0° C. Isopropyl magnesium chloride (14.0 ml, 2M-ether solution, 1.1 eq.) was added to the above mixture slowly and reacted for 10 minutes. After cooling the reaction mixture to −78° C., tert-butyl lithium (32.0 ml, 1.7M-heptane solution, 2.2 eq.) was added slowly and the reaction mixture was reacted for another 20 minutes. A solution of sulfur (800 mg, 25 mmol, 1.0 eq.) in anhydrous THF (30 ml) was added to the reaction mixture slowly and reacted until the temperature became 0° C. After 40 minutes, the temperature of the reaction mixture was adjusted at 0° C. and 5-chloromethyl-4-methyl-2-[(4-trifluoromethyl)phenyl]-thiazole of formula (VIII) (6.55 mg, 23.0 mmol, 0.9 eq.) dissolved in anhydrous THF (25 ml) was slowly added. The reaction mixture was reacted for around 30 minutes, followed by adding aqueous ammonium chloride solution (200 ml) to complete the reaction. The resultant organic layer was separated and dried over magnesium sulfate. The solvent was evaporated under reduced pressure. The residue was purified by silica gel column chromatography (hexane : ethyl acetate=3 : 1) to thereby yield 6.05 g of the title compound (yield: 68%)

Example 9

Preparation of 2-Methyl-4-[({4-methyl-2-[(4-trifluoromethyl)phenyl]thiazole-5-yl}methyl)sulfanyl]phenol [Step D]:

4-Iodo-2-methylphenol (3.90 g, 16.7 mmol) was dissolved in anhydrous tetrahydrofuran (120 ml) under nitrogen atmosphere and the temperature was maintained at 0° C. Isopropyl magnesium chloride (9.17 ml, 2M-ether solution, 1.1 eq.) was added to the above mixture slowly and reacted for 10 minutes. After cooling the reaction mixture to −78° C., tert-butyl lithium (21.6 ml, 1.7M-heptane solution, 2.2 eq.) was added slowly and the reaction mixture was reacted for another 20 minutes. A solution of sulfur (534 mg, 17.0 mmol, 1.0 eq.) in anhydrous THF (15 ml) was added to the reaction mixture slowly and reacted until the temperature became 0° C. After 60 minutes, the temperature of the reaction mixture was adjusted at 0° C. and 5-bromomethyl-4-methyl-2-[(4-trifluoromethyl)phenyl]-thiazole of formula (VIII) (5.14 g, 15.0 mmol, 0.9 eq.) dissolved in anhydrous THF (12 ml) was added slowly. The reaction mixture was reacted for around 30 minutes, followed by adding aqueous ammonium chloride solution (150 ml) to complete the reaction. The resultant organic layer was separated and dried over magnesium sulfate. The solvent was evaporated under reduced pressure. The residue was purified by silica gel column chromatography (hexane:ethyl acetate=3:1) to thereby yield 5.85 g of the title compound (yield: 87%)

Example 10

Preparation of ethyl {2-methyl-4-[({4-methyl-2-(4-trifluoromethyl-phenyl)-thiazole-5-yl}methyl)sulfanyl]phenoxy}acetate [Step E]:

2-Methyl-4-{4-methyl-2-[(4-trifluoromethyl)phenyl]thiazole-5-yl methyl-sulfanyl}phenol (10.0 g, 25.0 mmol) obtained from Example 7 was dissolved in acetone (300 ml) including 5% water and potassium carbonate (8.0 g, 58.0 mmol, 2.3 eq.) was added thereto at room temperature. Ethyl bromoacetate (4.20 ml, 38.0 mmol, 1.5 eq.) was added for 4 hours while stirring vigorously. After completion of reaction, the mixture was extracted with brine and ethyl acetate, and the organic layer was dried over magnesium sulfate. The solvent was evaporated under reduced pressure, and the residue was purified by silica gel column chromatography (hexane:ethyl acetate=5:1) to thereby yield 11.8 g of the title compound (yield: 98.5%).

$^1$H-NMR (300 MHz, CDCl$_3$): 7.97 (d, 2H, J=8.1 Hz), 7.66 (d, 2H, J=8.3 Hz), 7.21 (d, 1H, J=1.7 Hz), 7.12 (dd, 1H, J=8.4, 2.3 Hz), 6.60 (d, 1H, J=8.4 Hz), 4.62 (s, 2H), 4.24 (q, 2H, J=14.3, 7.1 Hz), 2.24 (s, 3H), 2.21 (s, 3H), 1.28 (t, 3H, J=7.1 Hz).

$^{13}$C-NMR (75.5 MHz, CDCl$_3$): 169.1, 163.0, 156.8, 136.5, 136.2, 132.5, 132.1, 131.1 (q, J=32 Hz), 130.6, 128.8, 126.8, 126.2 (q, J=4 Hz), 125.7, 122.4, 112.0, 66.0, 61.8, 32.9, 16.5, 15.2, 14.5

Example 11

Preparation of ethyl {2-methyl-4-[({4-methyl-2-(4-trifluoromethyl-phenyl)-thiazole-5-yl}methyl)sulfanyl]phenoxy}acetate [Step E]:

2-Methyl-4-{4-methyl-2-[(4-trifluoromethyl)phenyl]thiazole-5-yl methyl-sulfanyl}phenol (6.0 g, 15.0 mmol) obtained from Example 7 was dissolved in dimethyl sulfoxide (100 ml) including 5% water, and potassium carbonate (4.80 mg, 34.8 mmol, 1.5 eq.) was added thereto at room temperature. Ethyl bromoacetate (2.52 ml, 22.8 mmol, 1.5 eq.) was added for 1 hours while stirring vigorously at 50° C. After completion of reaction, the mixture was extracted with brine and ethyl acetate, and the organic layer was dried over magnesium sulfate. The solvent was evaporated under reduced pressure, and The residue was purified by silica gel column chromatography (hexane:ethyl acetate=5:1) to thereby yield 7.02 g of the title compound (yield: 98%).

Example 12

Preparation of 2-{2-methyl-4-[({4-methyl-2-[4-(trifluoromethyl)phenyl]-1,3-thiazole-5-yl}methyl)sulfanyl]phenoxy}acetic acid [Step F]:

Ethyl {2-methyl-4-[4-methyl-2-(4-trifluoromethyl-phenyl)-thiazole-5-yl sulfanyl]phenoxy}acetate obtained from Example 10 (5.0 g, 10.5 mmol) was dissolved in ethanol (200 ml) and 3N sodium hydroxide solution (35.0 ml) was added thereto. The reaction mixture was stirred for 30 minutes at room temperature. After completion of reaction, 2N HCl was added thereto for adjusting pH to be 2.0. Ethanol was evaporated by under reduced pressure and the reaction mixture was extracted with ethyl acetate and brine. Subsequently, the solvent was evaporated by under reduced pressure and the residue was purified by LH-20 column chromatography to thereby yield 4.71 g of the title compound (yield: 98.8%).

$^1$H-NMR (600 MHz, CD$_3$OD): 7.99 (d, 2H, J=8.2 Hz), 7.72 (d, 2H, J=8.2 Hz), 7.17 (d, 1H, J=2.1 Hz), 7.14 (dd, 1H, J=8.4, 2.1 Hz), 6.72 (d, 1H, J=8.4 Hz), 4.65 (s, 2H), 4.16 (s, 2H), 2.18 (s, 3H), 2.12 (s, 3H).

$^{13}$C-NMR (150.9 MHz, CD$_3$OD): 172.7, 164.8, 158.2, 152.6, 138.2, 137.5, 133.8, 133.3, 132.5 (q, J=33 Hz), 129.4, 127.8, 127.2 (q, J=4 Hz), 126.2, 112.9, 66.3, 32.9, 16.4, 14.8

INDUSTRIAL APPLICABILITY

As described above, thiazole derivatives of formula (I) can be prepared in a high yield easily, according to the present invention.

The invention claimed is:

1. A thiazole of formula (II) below:

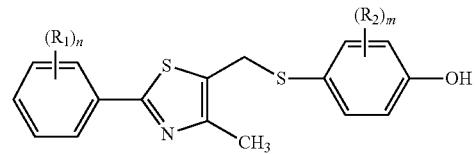

wherein,
R$_1$ represents a hydrogen atom, CF$_3$, or a halogen atom,
R$_2$ represents a hydrogen atom, a (C$_1$-C$_4$) alkyloxy, a (C$_1$-C$_4$) alkylthiooxy, a (C$_1$-C$_4$) alkylamine, a fluorine atom, or a chlorine atom,
m is an integer of 0 to 4, and
n is an integer of 0 to 5.

2. A thiazole of formula (IV) below:

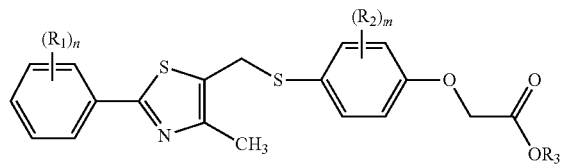

wherein:
R$_1$ represents a hydrogen atom, CF$_3$, or a halogen atom,
R$_2$ represents a hydrogen atom, a (C$_1$-C$_4$) alkyl, a (C$_1$-C$_4$) alkyloxy, a (C$_1$-C$_4$) alkylthiooxy, a (C$_1$-C$_4$) alkylamine, a fluorine atom, or a chlorine atom,
R$_3$ represents a propyl, an isopropyl, or a tert-butyl group as a protecting group of carboxyl acids,
m is an integer of 0 to 4, and
n is an integer of 0 to 5.

* * * * *